United States Patent
Purcell et al.

(10) Patent No.: US 7,984,716 B2
(45) Date of Patent: Jul. 26, 2011

(54) SELF-CONFORMING SOUND ATTENUATION EARPLUG

(75) Inventors: Ricky Wayne Purcell, Alpharetta, GA (US); Steven Craig Gehling, Cumming, GA (US); Waihong Leong, Roswell, GA (US); Anne Clare Moser, Chicago, IL (US); Sean S. Corbin, Morton Grove, IL (US); Scott Madison Belliveau, Plainfield, IL (US)

(73) Assignee: Kimberly-Clark Worldwide Inc., Neenah, WI (US)

( * ) Notice: Subject to any disclaimer, the term of this patent is extended or adjusted under 35 U.S.C. 154(b) by 22 days.

(21) Appl. No.: 11/821,390

(22) Filed: Jun. 22, 2007

(65) Prior Publication Data

US 2008/0314393 A1    Dec. 25, 2008

(51) Int. Cl.
*A61F 11/00* (2006.01)
*A61B 7/02* (2006.01)
*H04R 1/02* (2006.01)

(52) U.S. Cl. .......................... 128/865; 181/135; 381/328

(58) Field of Classification Search .................. 128/866, 128/867, 864–865; 181/129, 130, 134, 135; D24/106; 381/322, 328
See application file for complete search history.

(56) References Cited

U.S. PATENT DOCUMENTS

| | | |
|---|---|---|
| 3,618,600 A | 11/1971 | Douglass |
| 3,736,929 A | 6/1973 | Mills |
| 3,768,470 A | 10/1973 | Leight |
| 3,771,521 A | 11/1973 | Kittredge |
| 3,782,379 A | 1/1974 | Lampe |
| 3,800,791 A | 4/1974 | Visor |
| 3,811,437 A | 5/1974 | Gardner, Jr. |
| 3,872,559 A | 3/1975 | Leight |
| 3,881,570 A | 5/1975 | Lewis |
| 3,896,801 A | 7/1975 | Grout |
| 3,915,166 A | 10/1975 | McCrink |
| 4,053,051 A | 10/1977 | Brinkhoff |
| 4,060,080 A | 11/1977 | Akiyama |
| 4,089,332 A | 5/1978 | Rose |
| 4,094,315 A | 6/1978 | Leight |
| 4,143,657 A | 3/1979 | Takeda |
| 4,160,449 A | 7/1979 | Wade |
| 4,193,396 A | 3/1980 | Wacker |

(Continued)

FOREIGN PATENT DOCUMENTS

BE    886002 A    2/1981

(Continued)

OTHER PUBLICATIONS

American Society for Testing Materials (ASTM) Designation: D2856-94, "Standard Test Method for Open-Cell Content of Rigid Cellular Plastics by the Air Pycnometer," pp. 143-148, published May 1994.

(Continued)

*Primary Examiner* — Patricia M Bianco
*Assistant Examiner* — Ophelia Hawthorne
(74) *Attorney, Agent, or Firm* — Nancy M. Klembus

(57) ABSTRACT

A self-conforming sound attenuation earplug, including: a stem, at least one support joined with the stem and extending radially outward from the stem, and a shell engaging the support and encircling the stem to form a space between the shell and the stem. At least one of the support material and the shell material is a deformable-resilient material.

19 Claims, 4 Drawing Sheets

U.S. PATENT DOCUMENTS

| | | | |
|---|---|---|---|
| 4,215,683 | A | 8/1980 | Lundin et al. |
| 4,253,452 | A | 3/1981 | Powers et al. |
| 4,314,553 | A | 2/1982 | Westerdal |
| 4,344,425 | A | 8/1982 | Strauss |
| 4,434,794 | A | 3/1984 | Leight |
| 4,459,247 | A | 7/1984 | Rothemund |
| 4,461,290 | A | 7/1984 | Gardner, Jr. et al. |
| 4,498,469 | A | 2/1985 | Csiki |
| 4,582,053 | A | 4/1986 | Wilson |
| 4,702,238 | A | 10/1987 | Scott |
| 4,774,938 | A * | 10/1988 | Leight ............... 128/864 |
| 4,806,186 | A | 2/1989 | Sirkin et al. |
| 4,867,149 | A | 9/1989 | Falco |
| 4,896,679 | A | 1/1990 | St. Pierre |
| 4,936,411 | A | 6/1990 | Leonard |
| 5,044,463 | A | 9/1991 | Carr |
| 5,074,375 | A | 12/1991 | Grozil |
| 5,113,967 | A | 5/1992 | Killion et al. |
| 5,119,833 | A | 6/1992 | Powers |
| 5,153,387 | A | 10/1992 | Zwislocki et al. |
| 5,188,123 | A | 2/1993 | Gardner, Jr. |
| 5,249,309 | A | 10/1993 | Berg et al. |
| 5,452,731 | A | 9/1995 | Dickman |
| 5,467,784 | A | 11/1995 | Mobley et al. |
| 5,483,027 | A | 1/1996 | Krause |
| 5,557,077 | A | 9/1996 | Berg |
| 5,573,015 | A | 11/1996 | Williams |
| 5,581,821 | A | 12/1996 | Nakano |
| 5,668,354 | A | 9/1997 | Falco |
| 5,711,313 | A | 1/1998 | Fleming |
| 5,727,566 | A | 3/1998 | Leight |
| 5,811,742 | A | 9/1998 | Leight |
| 5,936,208 | A | 8/1999 | Hamery |
| 5,957,136 | A | 9/1999 | Magidson et al. |
| 5,988,313 | A | 11/1999 | H.ang.kansson |
| 6,006,857 | A * | 12/1999 | Leight et al. ............... 181/135 |
| 6,082,485 | A | 7/2000 | Smith |
| 6,105,715 | A | 8/2000 | Knauer |
| 6,129,175 | A | 10/2000 | Tutor et al. |
| 6,148,821 | A | 11/2000 | Falco |
| 6,241,041 | B1 | 6/2001 | Leight |
| 6,241,042 | B1 | 6/2001 | Falco |
| 6,256,396 | B1 | 7/2001 | Cushman |
| 6,264,870 | B1 | 7/2001 | H.ang.kansson |
| 6,286,622 | B1 | 9/2001 | Tiemann |
| 6,364,052 | B1 | 4/2002 | McLean |
| 6,408,981 | B1 | 6/2002 | Smith et al. |
| 6,425,398 | B1 | 7/2002 | Hirshfeld |
| 6,427,800 | B1 | 8/2002 | Hiselius et al. |
| 6,484,726 | B1 | 11/2002 | Remer et al. |
| D472,627 | S | 4/2003 | Falco |
| 6,568,394 | B2 | 5/2003 | Falco |
| 6,568,395 | B2 | 5/2003 | Tiemens |
| 6,659,103 | B2 * | 12/2003 | Tiemens ............... 128/864 |
| 6,691,822 | B2 | 2/2004 | Meussen et al. |
| 6,695,093 | B1 * | 2/2004 | Falco ............... 181/135 |
| 6,761,173 | B1 | 7/2004 | Kuno et al. |
| 6,920,956 | B1 | 7/2005 | Falco |
| 6,938,622 | B2 | 9/2005 | Huang |
| 6,981,504 | B2 | 1/2006 | Jenkins, Jr. |
| 7,025,061 | B2 | 4/2006 | Haussmann |
| 7,096,872 | B2 | 8/2006 | Ligon, Sr. et al. |
| 7,107,993 | B2 * | 9/2006 | Magidson ............... 128/864 |
| 7,475,686 | B2 * | 1/2009 | Knauer et al. ............... 128/864 |
| 2002/0124851 | A1 | 9/2002 | Knauer et al. |
| 2002/0153192 | A1 | 10/2002 | Falco et al. |
| 2003/0029459 | A1 | 2/2003 | Tiemens |
| 2003/0075185 | A1 | 4/2003 | Ulbrich |
| 2004/0045558 | A1 | 3/2004 | Taylor et al. |
| 2004/0069310 | A1 * | 4/2004 | Falco ............... 128/864 |
| 2004/0129276 | A1 | 7/2004 | Kuno et al. |
| 2005/0039761 | A1 | 2/2005 | Jenkins |
| 2005/0056289 | A1 | 3/2005 | Jenkins et al. |
| 2005/0094835 | A1 | 5/2005 | Doty |
| 2005/0135650 | A1 | 6/2005 | Berger |
| 2005/0229938 | A1 | 10/2005 | Jenkins |
| 2005/0274568 | A1 | 12/2005 | Falco et al. |
| 2006/0081415 | A1 | 4/2006 | Knauer et al. |
| 2006/0118124 | A1 | 6/2006 | Woo et al. |
| 2006/0213524 | A1 | 9/2006 | Woo et al. |
| 2006/0272649 | A1 | 12/2006 | Fleming |
| 2006/0278468 | A1 | 12/2006 | Bruck |
| 2007/0221232 | A1 * | 9/2007 | Jenkins ............... 128/864 |

FOREIGN PATENT DOCUMENTS

| | | |
|---|---|---|
| DE | 02 68 345 C1 | 1/1900 |
| EP | 0 036 422 B1 | 8/1983 |
| EP | 0 059 912 B1 | 2/1985 |
| EP | 0 108 728 B1 | 5/1988 |
| EP | 0 298 956 B1 | 8/1990 |
| EP | 0 244 979 B1 | 9/1990 |
| EP | 0 487 716 B1 | 9/1995 |
| EP | 1 192 920 A1 | 4/2002 |
| EP | 0 786 241 B1 | 7/2003 |
| EP | 0 836 840 B1 | 12/2003 |
| EP | 1 006 968 B1 | 1/2004 |
| EP | 1 276 443 B1 | 3/2006 |
| EP | 1 629 809 A1 | 3/2006 |
| JP | 2004-187745 A | 7/2004 |
| WO | WO 91/03218 A1 | 3/1991 |
| WO | WO 95/15067 A1 | 6/1995 |
| WO | WO 98/07296 A1 | 2/1998 |
| WO | WO 98/25558 A1 | 6/1998 |
| WO | WO 00/45760 A1 | 8/2000 |
| WO | WO 01/76519 A1 | 10/2001 |
| WO | WO 02/09614 A2 | 2/2002 |
| WO | WO 02/15829 A1 | 2/2002 |
| WO | WO 02/43633 A1 | 6/2002 |
| WO | WO 03/063744 A2 | 8/2003 |
| WO | WO 2004/028422 A1 | 4/2004 |
| WO | WO 2004/039296 A2 | 5/2004 |
| WO | WO 2004/066895 A1 | 8/2004 |
| WO | WO 2004/075774 A2 | 9/2004 |
| WO | WO 2004/100608 A2 | 11/2004 |
| WO | WO 2005/025796 A1 | 3/2005 |
| WO | WO 2005/120131 A2 | 12/2005 |
| WO | WO 2006/078767 A1 | 7/2006 |
| WO | WO 2006/084172 A1 | 8/2006 |

OTHER PUBLICATIONS

American Society for Testing Materials (ASTM) Designation: D3574-05, "Standard Test Methods for Flexible Cellular Materials—Slab, Bonded, and Molded Urethane Foams," pp. 1-25, published Aug. 2005.

"How Foam Firmness Affects Performance," *In Touch®—Information on Flexible Polyurethane Foam*, vol., No. 3, published by Polyurethane Foam Association, Jul. 1994, pp. 1-3.

"Pura-Cones™ Foam Earplugs," Moldex-Metric, Inc., Culver City, CA, Internet web page "http://www.moldex.com/foamplugprod/puracones.htm", viewed and printed Jun. 20, 2007.

"Traffic Cones® Foam Earplugs," Moldex-Metric, Inc., Culver City, CA, Internet web page "http://www.moldex.com/foamplugprod/trafficcones.htm", viewed and printed Jun. 20, 2007.

Patent Cooperation Treaty Search Report from the International Search Authority, International Application No. PCT/IB2008/051760 dated Nov. 3, 2008.

* cited by examiner

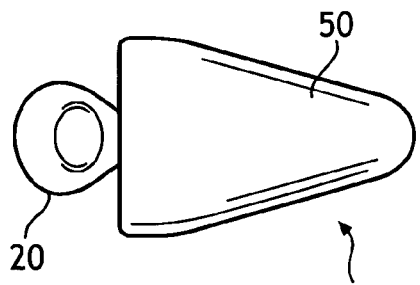
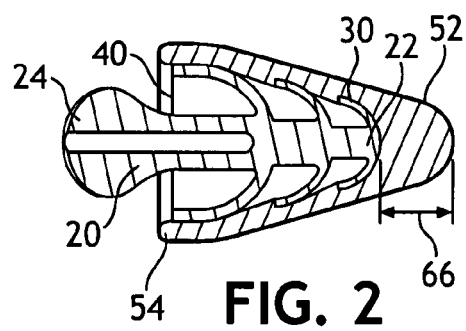
FIG. 1
FIG. 2
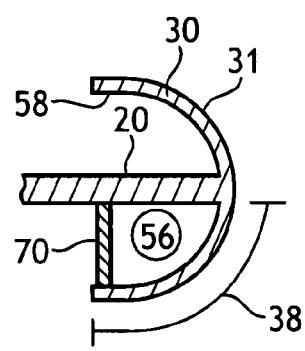
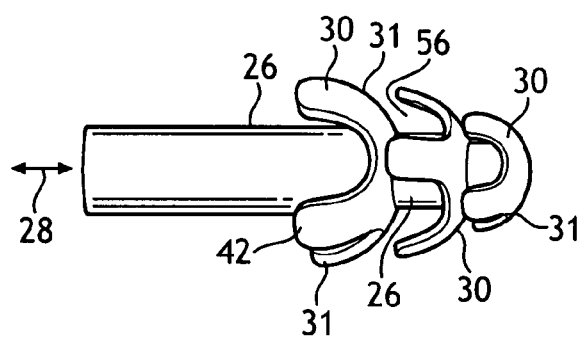
FIG. 3
FIG. 4
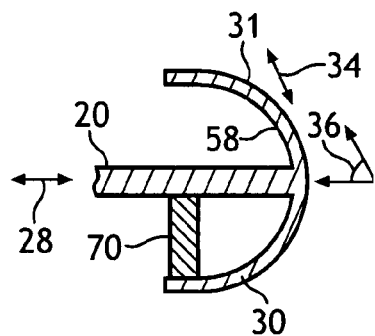
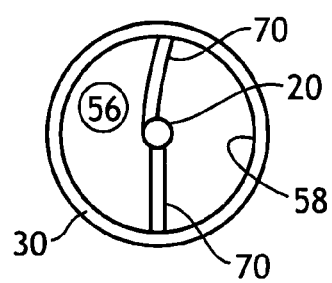
FIG. 5
FIG. 6

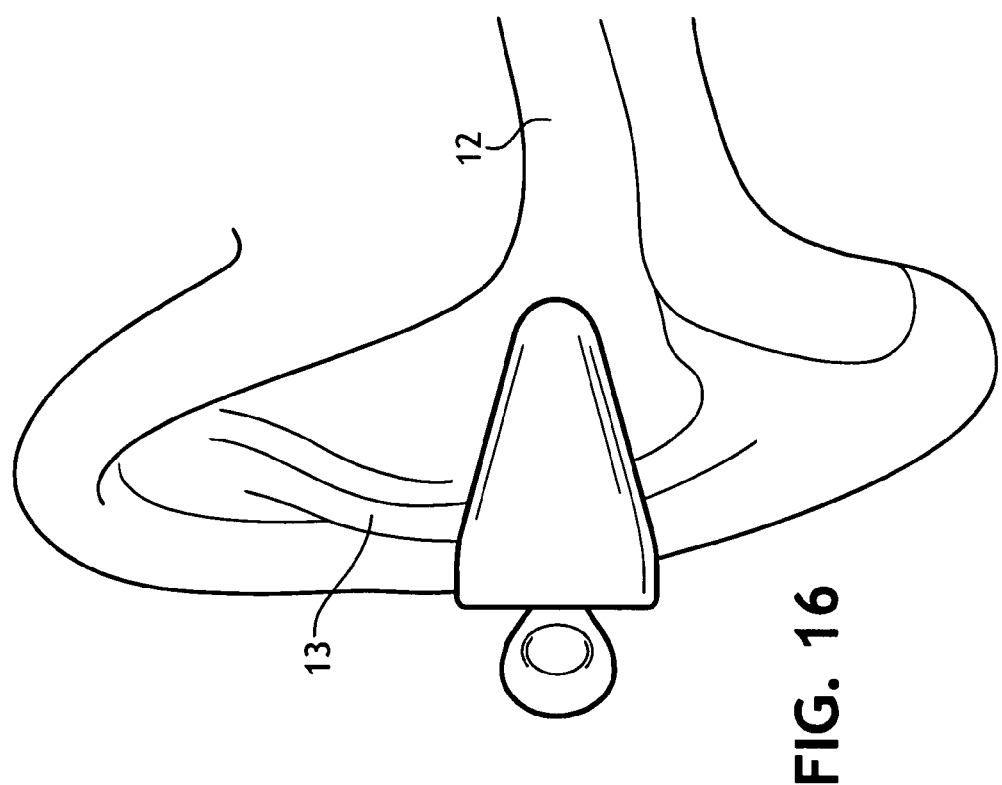

SELF-CONFORMING SOUND ATTENUATION EARPLUG

BACKGROUND OF THE INVENTION

The present invention relates generally to devices for location in an ear canal, and more particularly to earplugs that are insertable, self-conforming and used for noise reduction, e.g., high sound attenuation.

The need for adequate hearing protection in high noise environments has long been recognized among those concerned with health and safety issues, and much effort has gone into providing such protection. However, most experts in this field would acknowledge that this effort has not been completely successful. Protective devices have proliferated yet remain mediocre in performance, particularly in terms of a comfortable fit over a longer period of time (e.g., at least 4 hours). Workers in high noise environments who should use these devices often do not, or use them only under duress from their employers, and then do so improperly because they value comfort over a proper, likely uncomfortable, fit. Individuals that work in high noise environments rarely understand that the effects of high noise exposure are not limited to the moment but are cumulative as well. The lack of worker compliance with safety rules is exacerbated by the fact that currently available hearing protection devices are often uncomfortable, clumsy to use, and/or perform poorly due to improper insertion in the ear canal. Additionally, human ear canal sizes vary from 7 to 8 millimeters in diameter for "small" canals, to 9 to 10 millimeters in diameter for "medium" canals, to 11 to 12 and as much as 14 millimeters for "large" canals. Fortunately, as hearing protection devices become more comfortable and/or fit better across a broader range of canal sizes, worker compliance with their use should also improve.

For example, existing disposable roll-down foam earplugs can be uncomfortable when worn over longer periods of time, are difficult to properly insert, and/or do not readily stay in place for a longer period of time. Common disposable foam earplugs require the user to compress the area of the plug and insert it into the ear canal where it then attempts to re-expand. This method can cause discomfort for people with ear canals that are not the largest ones contemplated for that earplug's intended use, in that the more compressed the earplug in an ear sized smaller than "large", the greater the earplug's exerted outward force toward re-expansion. Such a roll-down type earplug may be found, for example, in U.S. Pat. No. 6,105,715 to Knauer.

Further, existing disposable foam earplugs require the user to roll the foam between their fingers to compress the foam to a sufficient size for proper insertion. If this step is not done, or is insufficiently done, the earplug is often inserted improperly (i.e., usually meaning not inserted enough into the ear canal) so as to not provide optimal protection (i.e., not optimal often being as little as 25% of the earplugs' advertised Noise Reduction Rating ("NRR") as determined by industry standards). And, even when the earplug is initially inserted properly, it is common for workers in a work environment that requires continuous earplug use to experience discomfort from the pressure exerted from the residual expansion forces of the rolled earplug. The discomfort is sometimes relieved by the partial removal of the earplug from the ear canal, thereby compromising the sound attenuating protection of the device. Also, if the user has dirty hands when compressing the earplug, dirt and/or germs are then put into the ear canal with the inserted earplug.

As with roll-down type earplugs, push-in type earplugs attenuate sound by causing an occlusion within the ear canal, thus obstructing the passage of sound there-through. Push-in type earplugs generally comprise an attenuating annular portion and a rigid to semi-rigid stem portion typically extending therefrom or embedded therein and used as an insertion means. The sound attenuating portion is typically of a soft compressible material. The rigid to semi-rigid portion may be composed of any material with sufficient rigidity as required to overcome the insertion pressure of the earplug. To insert the push-in type earplug, the user grasps the rigid/semi-rigid portion (or an end of the earplug proximate thereto), positions the earplug proximate the ear canal opening, and inserts the sound attenuating portion into the canal by pushing with the rigid/semi-rigid portion. The sound attenuating portion compresses, as necessary, upon entry into the ear canal and is held therein by a friction fit, occluding the canal and providing sound attenuation. Such a push-in type earplug may be found, for example, in U.S. Pat. Nos. 4,867,149 and 5,188,123 to Falco and Gardner Jr., respectively Push-in type earplugs are considered by many to provide easier insertion than other types of plugs. As discussed above, the wearer simply grasps the rigid or semi-rigid portion (or the end of the earplug proximate thereto) and inserts the sound attenuating portion at the opposite end into the ear canal, lodging the earplug therein and, hence, occluding the canal. However, while allowing a simplistic insertion, the push-in type ear plug typically does not yield the higher attenuations often provided by roll-down type earplugs. This may be because the push-in plug typically has a lesser surface area contacting the ear canal when inserted therein, or perhaps because the push-in plug wrinkles or folds during insertion creating leaks, or, further, because the push-in plug does not stay firmly in place during use and backs slightly out of the ear canal.

Therefore, existing roll-down and push-in type earplug materials and constructions do not have the ability to simultaneously accommodate each of: adequate insertion means, comfortable fit and sound attenuation. Accordingly, a hearing protection device is needed which is easy to insert, comfortable to the user during a longer period of use, and provides desired sound attenuation. The applicants have surprisingly invented such a device, as discussed further herein.

SUMMARY OF THE INVENTION

Various definitions used throughout the specification and claims are provided first, followed by a description of various aspects of the invention.

As used herein, "deformable-resilient" means the property of a material or composite material that permits it to be deformed in size and/or shape: (i) to 70% or less of its original size and/or shape by a sufficiently large force applied to cause deformation and (ii) then such recovers at least about 80% of its original size and shape no later than two minutes after removal of the force causing the deformation.

As used herein, "non-resilient" means the opposite of resilient.

As used herein, "Softness Rating" means the Indentation Force Deflection ("IFD") value for a flexible cellular material as determined using the standardized test method described in ASTM-D-3574, American Society for Testing and Materials, 2005, Test $B_1$—Indentation Force Deflection Test—Specified Deflection. The flexible cellular material used to construct the shell material of the invention is made into 5 test samples, each being a flat piece of foam having dimensions of 380 millimeters wide by 380 millimeters long by 100 millimeters thick. Each sample is tested according to the test method to determine its IFD in pounds per square inch (psi) and its equivalent measures in other scales, at 25% deflection. In the test, each sample is preflexed to 75% of its thickness at 230 millimeters/min, and then allowed to rest with the flex force removed, for six minutes. For the measured test then, the preflexed sample is indented at 50 millimeters/min to 25% of its total thickness and the force in newtons observed at that deflection after 60 seconds. The average of the IFD values for the five samples is the Softness Rating for that shell material.

In one aspect of the present invention, there is provided a self-conforming sound attenuation earplug for location in an ear canal. The device includes a stem made of a stem material and having a stem ear end and an opposite stem user end. At least one support is joined with the stem and made of a resilient support material and has at least a part of the support located between the stem ear end and the stem user end, where the support extends radially outward from the stem. A shell is made of a shell material and engages an outer circumference of at least a portion of the support and encircles at least a portion of the stem. A space is formed between an inner circumference of the shell and an outer circumference of the stem. The shell has a shell ear end and an opposite shell user end, and a tapered exterior that increases in circumference when moving from the shell ear end to the shell user end. At least one of the support material and the shell material is a deformable-resilient material. The shell and the support are formed independent of one another and composed of a different type of material.

Other features of the invention relate to particular configurations and characteristics of the stem, support and the shell, each alone and in relation to each other. Still other features of the invention will be in part apparent and in part pointed out hereinafter as well as better understood by practice of the invention.

It is to be understood that both the foregoing general description and the following detailed description are exemplary and are intended to provide further explanation of the invention claimed. The accompanying drawings, which are incorporated in and constitute part of this specification, are included to illustrate and provide a further understanding of the earplug for location in an ear canal that is the present invention.

BRIEF DESCRIPTION OF THE DRAWINGS

FIG. 1 is a perspective view of the present invention;

FIG. 2 is a cross-sectional view of the device in FIG. 1;

FIG. 3 is a partial cross-sectional view of an alternative support of the present invention;

FIG. 4 is a perspective view of an alternative stem and support of the present invention;

FIG. 5 is a partial cross-sectional view of an alternative support of the present invention;

FIG. 6 is a top view of an alternative support of the present invention;

FIG. 16 is a perspective view of the device in FIG. 1 as it is about to be inserted in an ear canal.

Corresponding reference characters indicate corresponding parts throughout the drawings.

DETAILED DESCRIPTION

Figure 7:
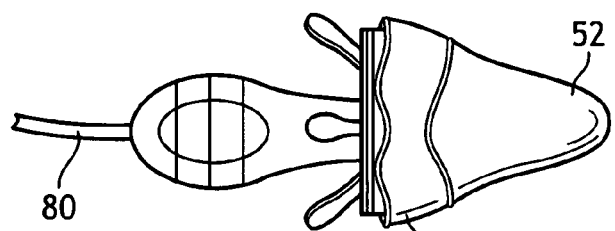
FIG. 7 is a side of an alternative configuration of the present invention.
Figure 8:
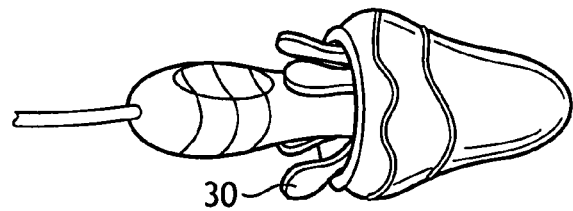
FIG. 8 is a perspective view of the device in FIG. 7.
Figure 9:
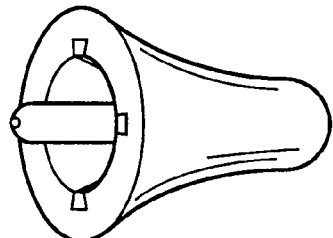
FIG. 9 is a perspective view of an alternative configuration of the present invention.
Figure 10:
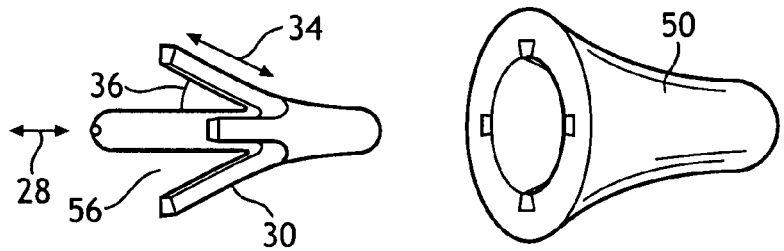
FIG. 10 is an exploded view of the device in FIG. 9.
Figure 11:
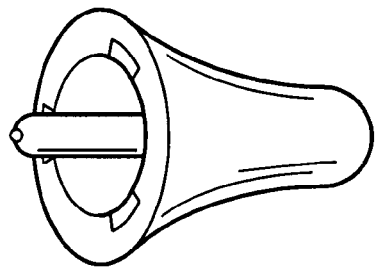
FIG. 11 a perspective view of an alternative configuration of the present invention.

Referring now to the drawings and in particular FIGS. 1-4 and 16 for example, there is depicted a earplug 10 for location in an ear canal 12. Particularly in FIG. 16, there is seen outer ear 13 joined to the portion of the ear canal 12 through which the device 10 is inserted for use, and where the ear drum (not seen) is located at the other end of the ear canal spaced from the device when inserted into the ear canal. Device 10 includes a stem 20, a support 30, and a shell 50. Stem 20 is made of a stem material and includes a stem ear end 22 and an opposite stem user end 24.

At least one support 30 is joined with stem 20, and advantageously, two, three, four, or more supports. Support 30 is made of a resilient support material, and at least a part of the support is located between the stem ear end 22 and the stem user end 24, relative to a side portion of the stem along the stem longitudinal axis 28. The support extends radially outward from the stem. Support 30 and stem 20 could be formed together of one material (e.g., most of the Figures), or formed of separate materials that are sequentially formed together (e.g., sequential injection molding steps, not specifically shown), or formed separately and then joined together by any conventional means (e.g., FIGS. 13-15), such as, adhesive, chemical or heat or other similarly resulting mechanical bonded relationship.

A shell 50 made of a shell material engages an outer circumference 31 of at least a portion of the support. The shell also encircles at least a portion of the stem, often not directly but relative thereto, and a space 56 is formed between an inner circumference 58 of the shell and an outer circumference 26 of the stem. The shell 50 has a shell ear end 52, an opposite shell user end 54, and a tapered exterior that increases in circumference when moving from the shell ear end 52 to the shell user end 54.

The following two features of the device, in combination with other requirements of the invention as discussed herein, are critical to it achieving its advantageous use over existing in-ear located earplug devices, and in particular attaining the proper balance of fit, comfort and sound attenuation, for enhanced user compliance over longer periods of time. First, at least one of the support material and the shell material is a deformable-resilient material. And second, the shell and the support are formed independent of one another and composed of a different type of material.

Without being limited to a theory of understanding, these combined features allow each of the shell and the support to do what they do best, and not make one perform a contradictory role. The applicants have inventively discovered that the ability to effectively seal the ear canal with a hearing protection device is related to the ability (i) to keep the earplug surface in continuous contact with the ear canal as the earplug is reduced in size during insertion and (ii) to conform the earplug surface to the irregularly shaped ear canal. The resistance to deformation by the earplug will determine how much force is therefore generated from the dimensional reduction in at least a portion of the earplug shape and/or size as it is inserted into the ear canal. The resistance to deformation is due to the mechanical properties of the earplug material (e.g.

durometer, Softness Rating, and/or density) as well as the physical cross sectional shape of the earplug components.

More specifically, and as embodied in the present invention like never before possible, shell 50 can now more so operate as a soft, cover-like material that itself exerts more limited outward pressure on ear canal 12, thereby enabling it to be tailored to addressing the comfort needs of device 10. For example, shell 50 can help to disperse the local forces of the adjacent support over a broader area thus minimizing the actual force transmitted by the support on any particular point of the ear canal. Also, shell 50 can serve as a cushion against the ear canal which provides comfort for the earplug that is resting against the ear canal over longer periods of use. Still further, shell 50 can act as a gap filler within the ear canal to create a better seal between the earplug and the ear canal.

Complementarily, support 30 made of resilient material now more so operates as a supportive member to the shell. The support 30 provides additional shape integrity for the shell and through this the radially outward force of the support enables a more consistent force profile to the overall device both before and when located in ear canal 12. This can also enhance sealing of the shell against the ear canal when in the ear canal, thereby enabling it to be tailored to addressing the fit needs of device 10 in a more comfortable way.

Further in this regard, though not required, there are other ways to enhance the just discussed features. For example, at least a portion of the support and the shell may be in an independent relationship relative to each other. While shell 50 must in some areas be more permanently joined with support 30 and/or stem 20 so the device stays together as a single unit, shell 50 can be joined such that at least a portion of the outer circumference 31 of the support can move relative to the adjacent inner circumference 58 of the shell when shell 50 is engaged with support 30. As another example, the support may continuously exert a radial outward force upon the shell where so engaged with the shell both before and when the device is located in the ear canal. As yet another example, the shell material may have a shell Softness Rating that is between 0.3 psi [0.02 Kg/cm$^2$] and 10.0 psi [0.73 Kg/cm$^2$]. Advantageously, though not required, the Softness Rating could be, in order of increased softness (and thus preference), between 0.3 psi [0.02 Kg/cm$^2$] and 7 psi, and between 0.3 psi [0.02 Kg/cm$^2$] and 4.0 psi [0.29 Kg/cm$^2$]. Through each of these additional features, the support can provide even better customized sealing of the shell against the ear canal and enhance fit, while also allowing the shell to maintain comfort needs.

As yet another example, there is the positioning of support 30 relative to stem 20. As seen in FIGS. 1-6 and particularly 5 for discussion here, the support can have support longitudinal axis 34 and the stem can have stem longitudinal axis 28, such that angle 36 is formed between the two axes in the range of, and in increasing advantage increments of, 50 degrees to 90 degrees, 60 degrees to 80 degrees, or 65 degrees to 75 degrees. As see in FIGS. 7-15 and particularly 10 for discussion here, the support can have support longitudinal axis 34 and the stem can have stem longitudinal axis 28, such that angle 36 is formed between the two axes in the range of, and in increasing advantage increments of, 10 degrees to 40 degrees, 15 degrees to 35 degrees, or 20 degrees to 30 degrees.

Figure 12:
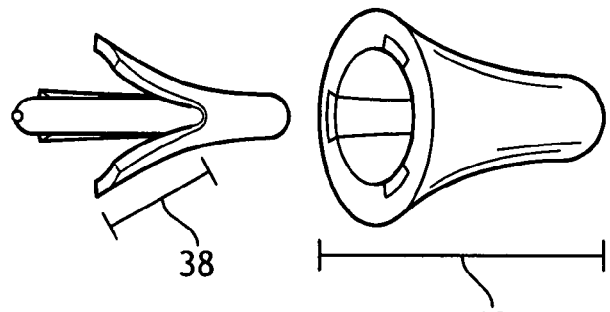
FIG. 12 is an exploded view of the device in FIG. 11.

As still another example, the device may include features related to support and shell lengths. Referring to FIGS. 3 and 12 for example, there is seen the support with a support length 38 and the shell with a shell length 68. The support length is measured from the outmost tip of the support to where the support joins the stem. The shell length is measured from its most distal end points of shell ear end 52 to shell user end 54. The support length can be greater than the shell length. Alternatively, the support length can be at most one-half that of the shell length.

As yet another example, the device may include features related to the shell thickness which can provide additional comfort when inserting and/or using device 10. Referring to FIG. 2, for example, at least one of the support member and the shell member may have a portion that is a continuous annular cross section ring positioned around and orthogonal to the stem longitudinal axis. When such ring is the shell, the ring (i.e., the wall of the shell located any where between the shell user end and the shell ear end), may have a radial thickness between 0.5 millimeters and 4 millimeters, more advantageously between 1.0 millimeters and 3.0 millimeters, and yet more advantageously between 1.5 millimeters and 2.0 millimeters. Additionally or alternatively, the shell material may be a wall of substantially uniform thickness from the shell user end to adjacent the shell ear end, and the shell ear end at 66 may have a thickness in the range of 2 millimeters to 10 millimeters in front of the stem ear end. This shell ear end thickness at 66 is measured relative to stem longitudinal axis 28 from the front most tip of stem ear end 22 to the front most tip of shell ear end 52. Still more advantageous in this regard, the shell ear end thickness at 66 may be in the range of 4 millimeters to 8 millimeters.

In other aspects of the invention there is provided various configurations for support 30. Referring to FIGS. 1-2 for example, support 30 can be a continuous cup-shaped member 40. Seen in FIG. 4 for example, the support can be a continuous cup-shaped member with at least one finger 42 extending from the cup-shaped member. Referring to FIGS. 1-2 again for example, support 30 can be continuous cup-shaped member 40 where the cup-shaped member has a spherical cross-sectional shape. In reference to FIGS. 3, 5 and 6 for example, at least one stiffening rib 70 can extend between support 30 and stem 20, and the rib can be planar as seen in FIG. 5.

The support can be made of a homogeneous material or a composite material, and may include one or more layers. Such materials may be polyurethane santoprene, polyethylene, or polypropylene, or other thermoplastic elastomer polymeric or other rubber or resilient material having a Shore A Durometer Hardness value between about 10 and about 90, and with a material thickness between about 0.20 millimeters and about 5 millimeters.

The stem may be made of the same type of materials as used for the support, for example, being composed of a deformable-resilient material having a shore A Durometer hardness value between about 10 and about 90, and with a stem material diameter between about 2 millimeters and about 8 millimeters.

The shell may be made of polyurethane santoprene, polyethylene, or polypropylene, or other thermo-plastic elastomer polymeric materials, hydro-entangled materials, air-entangled materials, paper materials such as tissue, toilet paper, or paper towels, waxed paper materials, coform materials, film or plastic materials such as those used to wrap food, or any other generally soft and pliable material that has the desired characteristics of the present invention. Furthermore, laminated or plied together multi-layer materials of two or more layers of any of the preceding materials may be employed. For example, the shell can be made of visco-elastic foam material which has various material properties. The density of the shell material can be about 6 to 20 lbm/ft$^3$ as measured by ASTM D-3574-05. More desirably, the density of the shell material can be about 10 to 15 lbm/ft$^3$. The foam can be further described by the cell size and desirably can have a minimum cell size >80 pores per inch and more desirably >100 pores per inch. The cell structure can be further defined by the cell structure which desirably can be between 30-70% open cells and more desirably between 40-60% open cells, as measured by Standard Test Method for Open-Celled Content of Rigid Cellular Plastics by the Air Pycnometer, ASTM 2856-94, American Society of Testing and Materials, Annual Book of ASTM Standards, 1998. The recovery time for the foam material can be desirably between 2 and 120 seconds, but more desirably between 2 and 20 seconds, as measured by a standard test for the recovery time that is found in ASTM 3574-05, previously cited. The water absorption of the foam can be desirably <20% and more desirably <5%, as measured by standard test methods such as found in ASTM D570.

Figure 13:
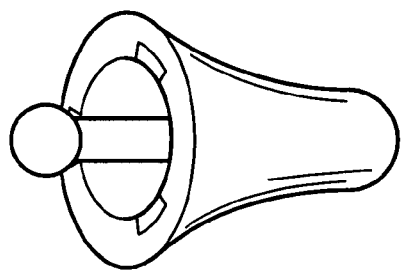
FIG. 13 is a perspective view of an alternative configuration of the present invention.
Figure 14:
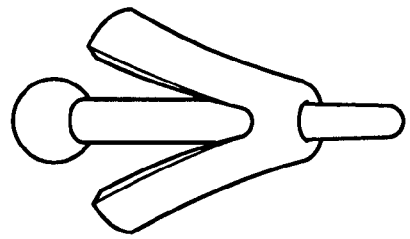
FIG. 14 is a perspective view of the support and stem of the device in FIG. 13.
Figure 15:
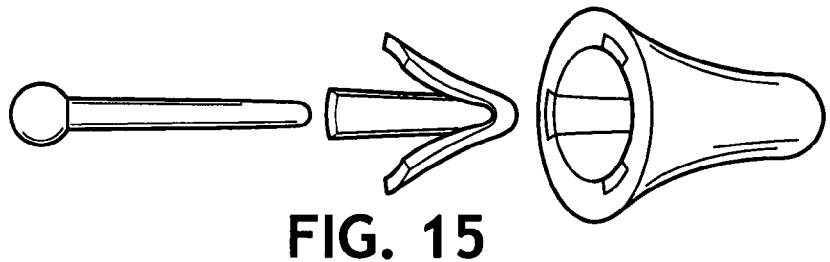
FIG. 15 is an exploded view of the device in FIG. 13.

Other aspects of the invention concern the construction of the stem and the support relative to one another. For example, and seen in FIGS. 2, 3 and 5, the stem and the support may be composed of the same type of material. Alternatively, as seen in FIGS. 13-15, the stem and the support can be each formed independently and then joined together in a fitted relationship.

Referring to FIG. 7, device 10 may include a lanyard 80 joined with stem 20, or other similar connection means for a variety of reasons, e.g., easy location when not in an ear canal, to help remove from the ear canal, to keep from falling into a user's work space, or the like.

In practice, device 10 may be used as follows. The user grasps the stem user end 24 (e.g., by a user's thumb and/or finger(s) or the like) and then locates the shell ear end adjacent the user's outer ear 13. The user then gently pushes the device into the ear canal 12 until is fits snuggly and yet is comfortable. So positioned in the ear canal, the device can perform sound optimization such as noise reduction and/or acoustic enhancement for the user, as desired. In particular, the final in-ear position is determined by the user's particular ear canal shape and size and is therefore self-conforming and customizable each time it is used. For removal, the user simply pulls the device out of their ear, with or without a slight twisting of the stem to aid in more gentle removal. Also, with the features of the present invention it is made of sufficiently substantial materials and design so as to allow for multiple uses.

While not required, it may be advantageous for sound enhancement, e.g., not only taking advantage of sound reduction capabilities but also hearing aid type capabilities. In this way, device 10 can be configured (not shown) to locate a microphone or the like in device 10 and help bring desired sound into the ear canal and/or locate a microphone in the ear canal better, e.g., via stem 20 and/or support 30.

As various changes could be made in the above constructions and methods, without departing from the scope of the invention, it is intended that all matter contained in the above description and shown in the accompanying drawings shall be interpreted as illustrative and not in a limiting sense.

When introducing elements of the invention or the preferred aspect(s) thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A self-conforming sound attenuation earplug comprising:
    a stem made of a stem material and having a stem ear end and an opposite stem user end;
    at least one support joined with the stem and made of a support material and having at least a part of the support located between the stem ear end and the stem user end;
    at least one stiffening rib extending between the support and the stem:
    a shell made of a shell material and engaging an outer circumference of at least a portion of the support and encircling at least a portion of the stem wherein a space is formed between an inner circumference of the shell and an outer circumference of the stem and the shell has a shell ear end and an opposite shell user end and a tapered exterior that increases in circumference when moving from the shell ear end to the shell user end and wherein the support material is a deformable-resilient material;
    wherein the shell and the support are formed independent of one another and composed of a different type of material, and wherein the support extends radially outward from the stem and over a portion of the stem, and
    wherein the stem material and the support material each comprise a deformable-resilient material having a Shore A Durometer Hardness value between about 10 and about 45.

2. The earplug of claim 1 wherein the support has a support longitudinal axis and the stem has a stem longitudinal axis and an angle in the range of 10 degrees to 90 degrees is formed between the two axes.

3. The earplug of claim 2, wherein the support has a support longitudinal axis and the stem has a stem longitudinal axis and an angle in the range of 10 degrees to 40 degrees is formed between the two axes.

4. The earplug of claim 3 wherein the support has the support longitudinal axis and the stem has a stem longitudinal axis and an angle in the range of 15 degrees to 35 degrees is formed between the two axes.

5. The earplug of claim 2 wherein the support has a support longitudinal axis and the stem has a stem longitudinal axis and an angle in the range of 60 degrees to 80 degrees is formed between the two axes.

6. The earplug of claim 1 wherein the shell material has a shell Softness Rating between 0.3 psi [0.02 Kg/cm$^2$] and 10.0 psi [0.73 Kg/cm$^2$].

7. The earplug of claim 6 wherein the shell material has a shell Softness Rating between 0.3 psi [0.02 Kg/cm$^2$] and 4.0 psi [0.29 Kg/cm$^2$].

8. The earplug of claim 1 wherein the first support comprises a continuous cup-shaped member.

9. The earplug of claim 1 wherein the support comprises a continuous cup-shaped member and the cup-shaped member has a spherical cross-sectional shape.

10. The earplug of claim 1 wherein the shell material comprises a wall of substantially uniform thickness from the shell user end to the shell ear end.

11. The earplug of claim 1 wherein the stem and the support are composed of the same type of material.

12. The earplug of claim 1 wherein the support material is a thermo-plastic elastomer polymeric material.

13. The earplug of claim 1 wherein the shell is formed of a cellular foam.

14. The earplug of claim 1 wherein the stem and the support are each formed independently and join together in a fitted relationship.

15. A self-conforming sound attenuation earplug comprising:
    a stem made of a stem material and having a stem ear end and an opposite stem user end;
    at least one support joined with the stem and made of a support material and having at least a part of the support located between the stem ear end and the stem user end;

a shell made of a shell material and engaging an outer circumference of at least a portion of the support and encircling at least a portion of the stem wherein a space is formed between an inner circumference of the shell and an outer circumference of the stem and the shell has a shell ear end and an opposite shell user end and a tapered exterior that increases in circumference when moving from the shell ear end to the shell user end and wherein the support material is a deformable-resilient material;

wherein the shell and the support are formed independent of one another and composed of a different type of material, and wherein the support extends radially outward from the stem and over a portion of the stem, and wherein the stem material and the support material each comprise a deformable-resilient material a Shore A Durometer Hardness value between about 10 and about 90.

16. The earplug of claim 15 wherein the shell material has a shell Softness Rating between 0.3 psi [0.02 Kg/cm$^2$] and 10.0 psi [0.73 Kg/cm$^2$].

17. The earplug of claim 16 wherein the shell material has a shell Softness Rating between 0.3 psi [0.02 Kg/cm$^2$] and 4.0 psi [0.29 Kg/cm$^2$].

18. The earplug of claim 15 wherein the support has a support longitudinal axis and the stem has a stem longitudinal axis and an angle in the range of 10 degrees to 90 degrees is formed between the two axes.

19. The earplug of claim 18 wherein the support has a support longitudinal axis and the stem has a stem longitudinal axis and an angle in the range of 60 degrees to 80 degrees is formed between the two axes.

* * * * *